(12) United States Patent
Wang

(10) Patent No.: US 11,724,041 B2
(45) Date of Patent: Aug. 15, 2023

(54) DRIVE MECHANISM AND MEDICAMENT DELIVERY DEVICE COMPRISING THE SAME

(71) Applicant: SHL MEDICAL AG, Zug (CH)

(72) Inventor: Hsuan Wang, Taoyuan (TW)

(73) Assignee: SHL MEDICAL AG, Zug (CH)

( * ) Notice: Subject to any disclaimer, the term of this patent is extended or adjusted under 35 U.S.C. 154(b) by 553 days.

(21) Appl. No.: 16/981,993

(22) PCT Filed: Feb. 28, 2019

(86) PCT No.: PCT/EP2019/054956
§ 371 (c)(1),
(2) Date: Sep. 17, 2020

(87) PCT Pub. No.: WO2019/185277
PCT Pub. Date: Oct. 3, 2019

(65) Prior Publication Data
US 2021/0106766 A1    Apr. 15, 2021

(30) Foreign Application Priority Data
Mar. 27, 2018  (EP) ..................................... 18164326

(51) Int. Cl.
*A61M 5/315*    (2006.01)
*A61M 5/31*    (2006.01)

(52) U.S. Cl.
CPC .... *A61M 5/31585* (2013.01); *A61M 5/31526* (2013.01); *A61M 5/31528* (2013.01);
(Continued)

(58) Field of Classification Search
CPC .......... A61M 5/31585; A61M 5/31526; A61M 5/31528; A61M 5/31568; A61M 2005/3126; A61M 2205/581
See application file for complete search history.

(56) References Cited

U.S. PATENT DOCUMENTS

2009/0247960 A1* 10/2009 Kohlbrenner ........... A61M 5/20
                                                                604/232
2017/0266385 A1*  9/2017 Farris ................ A61M 5/31581
(Continued)

FOREIGN PATENT DOCUMENTS

CN       105246532 A    1/2016
JP      2008-541802 A   11/2008
(Continued)

OTHER PUBLICATIONS

International Search Report and Written Opinion for Int. App. No. PCT/EP2019/054956, completed Mar. 20, 2019.

*Primary Examiner* — Dung T Ulsh
(74) *Attorney, Agent, or Firm* — McDonnell Boehnen Hulbert & Berghoff LLP

(57) ABSTRACT

A drive mechanism for a medicament delivery device is presented having an activation rod provided with external activation rod threads having a first thread helix angle, an activation knob rotationally locked with the activation rod, wherein the activation knob is configured to be moved between a first axial position relative to the activation rod in which the activation knob is prevented from rotation and a second axial position in which the activation knob is allowed to rotate in a first direction, an axially slidable drum which is rotationally locked, a dose drum rotationally locked relative to the activation rod, wherein the dose drum is configured to rotate relative to the slidable drum, an indicator drum provided with external indicator drum threads having a second thread helix angle, wherein rotation of the activation knob in the first direction causes concurrent first rotation of the activation rod and the dose drum in accordance with the first thread helix angle.

20 Claims, 5 Drawing Sheets

(52) U.S. Cl.
CPC . *A61M 5/31568* (2013.01); *A61M 2005/3126* (2013.01); *A61M 2205/581* (2013.01)

(56) References Cited

U.S. PATENT DOCUMENTS

2018/0015228 A1* 1/2018 Stefanov ............ A61M 5/31536
2018/0050159 A1* 2/2018 Enge ................. A61M 5/31553

FOREIGN PATENT DOCUMENTS

| | | |
|---|---|---|
| JP | 2012-510836 A | 5/2012 |
| JP | 2014-513588 A | 6/2014 |
| WO | 2006/058883 A2 | 6/2006 |
| WO | 2006/125328 A1 | 11/2006 |
| WO | 2010/063687 A1 | 6/2010 |
| WO | 2012/125876 A1 | 9/2012 |
| WO | 2013/058698 A1 | 4/2013 |
| WO | 2014/166909 A1 | 10/2014 |
| WO | 2017/106221 A1 | 6/2017 |

* cited by examiner

DRIVE MECHANISM AND MEDICAMENT DELIVERY DEVICE COMPRISING THE SAME

CROSS REFERENCE TO RELATED APPLICATIONS

The present application is a U.S. National Phase Application pursuant to 35 U.S.C. § 371 of International Application No. PCT/EP2019/054956 filed Feb. 28, 2019, which claims priority to European Patent Application No. 18164326.3 filed Mar. 27, 2018. The entire disclosure contents of these applications are herewith incorporated by reference into the present application.

TECHNICAL FIELD

The present disclosure generally relates to medical devices. In particular, it relates to a drive mechanism for a medicament delivery device and to a medicament delivery device comprising such a drive mechanism.

BACKGROUND

Manual medicament delivery devices such as insulin pens are widely used today. The dose to be injected is manually set by the user before injection.

An example of a medicament delivery device of this type is disclosed in WO2013058698 A1. This document discloses a medicament delivery device including a housing and a dose setting drum for setting a dose when rotated in a first direction and for delivering a dose when rotated in a second direction. When performing an injection, the user pushes a distal push button, wherein the force on the push button urges a dose activator knob in the proximal direction. This force is transferred to the dose setting drum, which due to its threaded connection with the housing causes the dose setting drum to rotate in the second direction.

The dose setting drum is provided with indicia shown in a window of the housing. The scale of this printing may be limited by the capability of the printing machines, meaning that the pitch of the dose setting drum threads will be dependent of the printing limitations. It is desired to design the dose setting drum threads to enable clear and precise dose setting. Additionally, the pitch may also affect the force that a user has to apply to perform an injection. The dose setting drum is thus designed taking these considerations into account.

SUMMARY

In view of the above, a general object of the present disclosure is to provide a drive mechanism and a medicament delivery device which solves or at least mitigates the problems of the prior art.

There is hence according to a first aspect of the present disclosure provided a drive mechanism for a medicament delivery device, comprising: an activation rod provided with external activation rod threads having a first thread helix angle, an activation knob rotationally locked with the activation rod, wherein the activation knob is configured to be moved between a first axial position relative to the activation rod in which the activation knob is prevented from rotation and a second axial position in which the activation knob is allowed to rotate in a first direction, an axially slidable drum which is rotationally locked, a dose drum rotationally locked relative to the activation rod, wherein the dose drum is configured to rotate relative to the slidable drum, an indicator drum provided with external indicator drum threads having a second thread helix angle, wherein rotation of the activation knob in the first direction causes concurrent first rotation of the activation rod and the dose drum in accordance with the first thread helix angle thereby axially displacing the activation knob, the activation rod, the dose drum and the slidable drum in a distal direction, wherein the slidabe drum is configured to bring the indicator drum with it causing second rotation of the indicator drum in accordance with the second thread helix angle.

The first thread helix angle controls the force necessary to apply to perform an injection and can thus be optimised to enable low force requiring and easy medicament administration. The second thread helix angle can be designed independently of the first thread helix angle and may be adapted to provide the best dose scaling possible. Hereto, these two functions of the drive mechanism may be optimised independently.

According to one embodiment the first thread helix angle is larger than the second thread helix angle. With a larger first thread helix angle the force necessary to perform medicament administration may be reduced, while with a smaller second thread helix angle the precision of the dose setting as well as printing in manufacturing may be optimised.

The major diameter of the activation rod may be smaller than the inner diameter of the indicator drum.

The external activation rod threads may have a first pitch and the external indicator drum threads may have a second pitch.

One embodiment comprises a remaining dosage ring provided with inner ring threads, wherein the dose drum is provided with external dose drum threads configured to cooperate with the inner ring threads, wherein the remaining dosage ring is rotationally locked with the slidable drum to prevent rotation of the remaining dosage ring relative to the slidable drum, causing the remaining dosage ring to move proximally along the external dose drum threads when the activation knob is rotated in the first direction. The remaining dosage ring provides a mechanical "memory" in the sense that its position along the dose drum is maintained after injection due to the dosage drum moving back proximally without rotation during medicament expulsion. The position of the remaining dosage ring will successively for each administered dose be moved proximally along the external dose drum threads until reaching the end of axially extending slits on the slidable drum, in which case the activation knob and activation rod will not be able to rotate in the first direction, indicating that no further dosage is available.

One embodiment comprises a plunger rod, and an insert member provided with a threaded insert member inner surface, wherein the plunger rod is configured to rotate only in the first direction, and wherein the insert member is coupled in a rotationally locked manner with the plunger rod and wherein the insert member is configured to receive a proximal end portion of the activation rod, wherein the external activation rod threads are configured to cooperate with the threaded insert member inner surface, causing the activation rod and dose drum to be axially displaced in the distal direction when the activation knob is rotated in the first direction.

The plunger rod may be hollow and configured to receive the activation rod. The insert member may have an axial through-opening which is provided with the threaded thread insert inner surface.

One embodiment comprises a thread insert provided with an threaded thread insert inner surface and configured to receive the plunger rod, wherein the plunger rod has external plunger rod threads configured to cooperate with the threaded thread insert inner surface, and a ratchet member configured to be rotationally locked with the plunger rod and to be received by the thread insert allowing rotation of the plunger rod only in the first direction.

According to one embodiment pushing of the activation knob when the activation knob has been axially displaced by rotation of the activation knob in the first direction causes the activation knob to obtain the first axial position, whereby the activation rod and the dose drum are configured to move in the proximal direction without rotation, causing the plunger rod to rotate in the first direction and thereby move in the proximal direction through the thread insert.

One embodiment comprises a ratchet ring configured to engage with the slidable drum to rotationally lock the ratchet ring relative to the slidable drum, wherein the ratchet ring is configured to engage with the activation knob in the first axial position to thereby prevent rotation of the activation knob and to disengage from the activation knob in the second axial position.

According to one embodiment the activation knob has an inner surface facing the activation rod, wherein the inner surface is provided with a first axial protrusion and the ratchet ring is provided with first teeth configured to engage with the first axial protrusion to prevent rotation of the activation knob in the first axial position.

According to one embodiment the ratchet ring has a distal edge and the first teeth are distributed along the distal edge.

According to one embodiment the activation knob and the ratchet ring are configured to engage with a snap-fit in the first axial position to maintain the activation knob in the first axial position.

According to one embodiment the activation knob is provided with second teeth along its inner perimeter surface and the ratchet ring comprises arms configured to engage with the second teeth to provide audible clicks when the activation knob is rotated in the first direction.

According to one embodiment the indicator drum has an external surface provided with a dosage scale.

One embodiment comprises a housing configured to receive the activation rod, the dose drum, the slidable drum and the indicator drum, wherein the housing has an inner surface provided with inner housing threads configured to cooperate with the external indicator drum threads and wherein the slidable drum is rotationally locked with the housing.

There is according to a second aspect of the present disclosure provided a medicament delivery device comprising: a housing, and a drive mechanism according to the first aspect arranged in the housing.

According to one embodiment the slidable drum is rotationally locked with the housing.

According to one embodiment the housing has an inner surface provided with inner housing threads configured to cooperate with the external indicator drum threads.

Generally, all terms used in the claims are to be interpreted according to their ordinary meaning in the technical field, unless explicitly defined otherwise herein. All references to "a/an/the element, apparatus, component, means, etc. are to be interpreted openly as referring to at least one instance of the element, apparatus, component, means, etc., unless explicitly stated otherwise.

BRIEF DESCRIPTION OF THE DRAWINGS

The specific embodiments of the inventive concept will now be described, by way of example, with reference to the accompanying drawings, in which.

DETAILED DESCRIPTION

The inventive concept will now be described more fully hereinafter with reference to the accompanying drawings, in which exemplifying embodiments are shown. The inventive concept may, however, be embodied in many different forms and should not be construed as limited to the embodiments set forth herein; rather, these embodiments are provided by way of example so that this disclosure will be thorough and complete, and will fully convey the scope of the inventive concept to those skilled in the art. Like numbers refer to like elements throughout the description.

The drive mechanism as well as the medicament delivery device disclosed herein has an elongate shape, with one end being a proximal end and the opposite end being a distal end. As used herein, the term "proximal end" refers to that end which during medicament administration faces the injection site, i.e. that end of the two ends which is closest to the injection site. This definition also extends to any internal or external component of the drive mechanism and the medicament delivery device, i.e. the proximal end of any component is that which is closest to the proximal end of the drive mechanism/medicament delivery device. With "proximal direction" is meant a direction from the distal end towards the proximal end, along the central axis of the drive mechanism/medicament delivery device. With "distal direction" is meant the opposite direction to "proximal direction".

Figure 1:
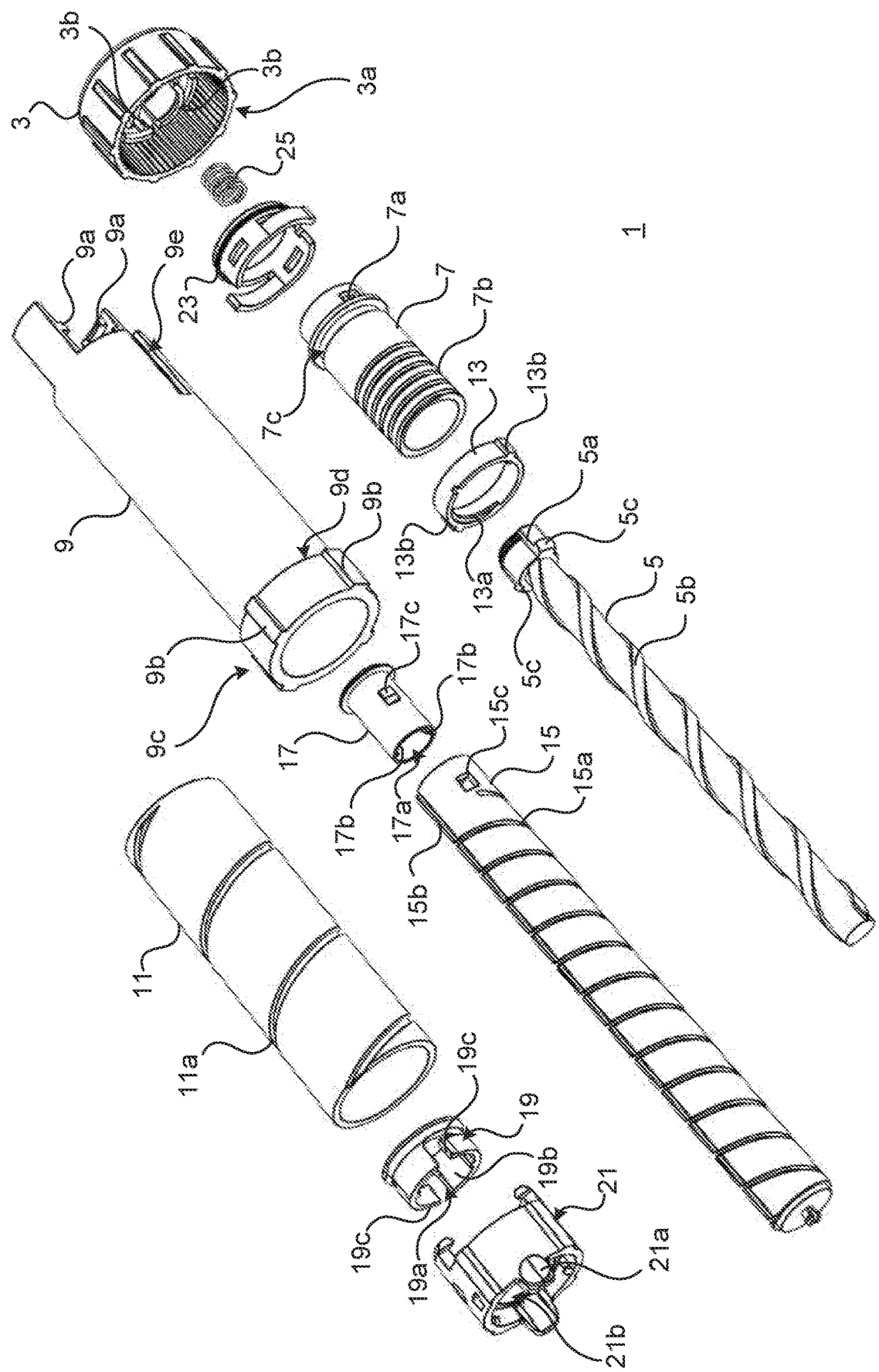
FIG. 1 shows an exploded view of an example of a drive mechanism for a medicament delivery device.

FIG. 1 is an explosive view of an example of a drive mechanism 1 for a medicament delivery device. The drive mechanism 1 comprises an activation knob or button 3, an activation rod 5, a dose drum 7 and a slidable drum 9.

The activation knob 3 forms a distal end of the drive mechanism 1. The activation knob 3 is configured to receive a distal end of the activation rod 5. The activation knob 3 and the activation rod 5 are configured to be rotationally locked with each other.

According to the present example, the activation rod 5 has lateral wings 5a extending radially outwards, which are configured to engage with the activation knob 3. The activation knob 3 has a central channel 3a opening from a proximal end of the activation knob 3. The central channel 3a is provided with oppositely arranged holding members 3b which extend axially around the distal end of the activation rod 5. The holding members 3b are configured to receive the lateral wings 5a between them to thereby rotationally lock the activation knob 3 with the activation rod 5.

The activation rod 5 is provided with external activation rod threads 5b. The external activation rod threads 5b extend from the proximal end to the distal end of the activation rod 5.

The dose drum 7 is configured to engage with the activation rod 5. The dose drum 7 is configured to be rotationally locked with the activation rod 5. Hereto, the distal end of the activation rod 5a has locking arms 5c extending radially outwards. The dose drum 7 is provided with corresponding openings 7a configured to engage with the locking arms 5c to thereby rotationally lock the dose drum 7 with the activation rod 5.

The dose drum 7 is provided with external dose drum threads 7b. The dose drum 7 furthermore has a circumferentially extending groove 7c.

The slidable drum 9 has a distal end provided with radially inwards extending protrusions 9a. The radially inwards extending protrusions 9a are configured to engage with the circumferentially extending groove 7c of the dose drum 7. The slidable drum 9 and the dose drum 7 are thereby axially locked relative to each other. This configuration allows for rotation of the dose drum 7 relative to the slidable drum 9. The dose drum 7 and the slidable drum 9 are hence configured to enable the dose drum 7 to rotate relative to the slidable drum 9.

The drive mechanism 1 may furthermore comprise a housing (not shown in FIG. 1). The slidable drum 9 may be configured to be rotationally locked with the housing. The slidable drum 9 may furthermore be configured to be able move or slide axially relative to the housing. According to the example in FIG. 1, the slidable drum 9 has an outer surface provided with axial ribs 9b. The housing may be provided with axial grooves configured to receive the axial ribs 9b to thereby rotationally lock the slidable drum 9 with the housing, and to allow axial displacement of the slidable drum 9 relative to the housing.

The slidable drum 9 has a proximal end portion 9c provided with a heel 9d which defines a step in the proximal direction.

The slidable drum 9 also has axially extending slits 9e. The axially extending slits 9e are provided at a distal end portion of the slidable drum 9. The axially extending slits 9e are in level with the external dose drum threads 7b. The axially extending slits 9e have an axial extension which is longer than the axial extension of the external dose drum threads 7b of the dose drum 7.

The drive mechanism 1 comprises an indicator drum 11. The indicator drum 11 is configured to receive the slidable drum 9. The indicator drum 11 has external indicator drum threads 11a. The housing is provided with corresponding inner housing threads configured to cooperate with the external indicator drum threads 11a. The indicator drum 11 is dimensioned so that its distal end face rests on the heel 9d of the slidable drum 9. Hereto, axial displacement of the slidable drum 9 in the distal direction causes the indicator drum 11 to follow the movement of the slidable drum 9.

The indicator drum 11 may have an external surface provided with a dose scale. The housing may have a window which shows the current dose set according to the dose scale.

The drive mechanism 1 comprises a remaining dosage ring 13 provided with inner ring threads 13a. The remaining dosage ring 13 is configured to be arranged around the dose drum 7. In particular, the inner ring threads 13a are configured to cooperate with the external dose drum threads 7b. The remaining dosage ring 13 is thereby able to move relative to the dose drum 7 from one end of the external dose drum threads 7b to the other end of the external dose drum threads 7b where the axially extending slits 9e are the stopper of the remaining dose ring 13.

The remaining dosage ring 13 has radially outwards extending protrusions 13b. The radially outwards extending protrusions 13b are configured to be received with essentially no circumferential play by a respective one of the axially extending slits 9e of the slidable drum 9. The remaining dosage ring 13 is hence rotationally locked with the slidable drum 9. The remaining dosage ring 13 is however able to move axially relative to the slidable drum 9.

The drive mechanism 1 comprises a plunger rod 15. The plunger rod 15 is provided with external plunger rod threads 15a. The plunger rod 15 furthermore comprises external axial grooves 15b extending along the length of the plunger rod 15. The plunger rod 15 is hollow and opens from the distal end thereof. The plunger rod 15 is configured to receive the activation rod 5 in its hollow interior.

The exemplified drive mechanism 1 also comprises an insert member 17. The insert member 17 is configured to be received by the plunger rod 15. In particular, the insert member 17 is located at a distal end portion of the plunger rod 15. The insert member 17 is configured to be rotationally locked with the plunger rod 15. Hereto, according to the present example, the insert member 17 has insert member protrusions 17c extending radially outwards and the plunger rod 15 has corresponding openings configured to receive respective insert member protrusions 17c to thereby rotationally lock the insert member 17 with the plunger rod 15.

The insert member 17 has an axial through-opening 17 which is provided with a threaded thread insert inner surface 17b. The insert member 17 is configured to receive the activation rod 5. Hereto, a proximal end portion of the activation rod 5 extends through the insert member 17 and into the plunger rod 15. The threads of the threaded thread insert inner surface 17b are designed to cooperate with the external activation rod threads 5b.

The exemplified drive mechanism 1 comprises a ratchet member 19 and a thread insert 21 configured to cooperate with the ratchet member 19. The thread insert 21 is configured to be rotationally locked with the housing. Hereto, the exemplified thread insert 21 is provided with radially outwards extending structures 21a configured to engage with the housing which is provided with corresponding openings configured to receive the radially outwards extending structures 21a.

The thread insert 21 has an axial through-opening 21b having a first section having a first diameter configured to receive the ratchet member 19 and a second section having a second diameter smaller than the first diameter. The first section has an inner surface provided with a plurality of ratchet teeth. The second section has a threaded thread insert inner surface. The threads of the threaded thread insert inner surface are configured to cooperate with the external plunger rod threads 15a.

The ratchet member 19 has a central through-opening 19a configured to receive the plunger rod 15. The ratchet member 19 has radially inwards extending engagement structures 19b configured to engage with a respective one of the axial grooves 15b of the plunger rod 15. The plunger rod 15 and the ratchet member 19 are thereby rotationally locked with each other. The ratchet member 19 is provided with ratchet arms 19c configured to cooperate with the ratchet teeth of the thread insert 21. In particular, the ratchet member 19 is able to rotate in one direction inside the thread insert 21 and prevented from rotating in an opposite direction. Further details regarding the operation and structure of the ratchet member 19 and thread insert 21 may be found in WO 2013/058698, which is hereby incorporated by reference.

The drive mechanism 1 also comprises a ratchet ring 23. The ratchet ring 23 is configured to engage with the slidable drum 9 to thereby rotationally lock the ratchet ring 23 with the slidable drum 9. The ratchet ring 23 is hence also rotationally locked relative to the housing.

Additionally, the drive mechanism 1 may also comprise a resilient member 25 such as a spring, configured to bias the activation rod 5 away from the activation knob 3.

Figure 2:
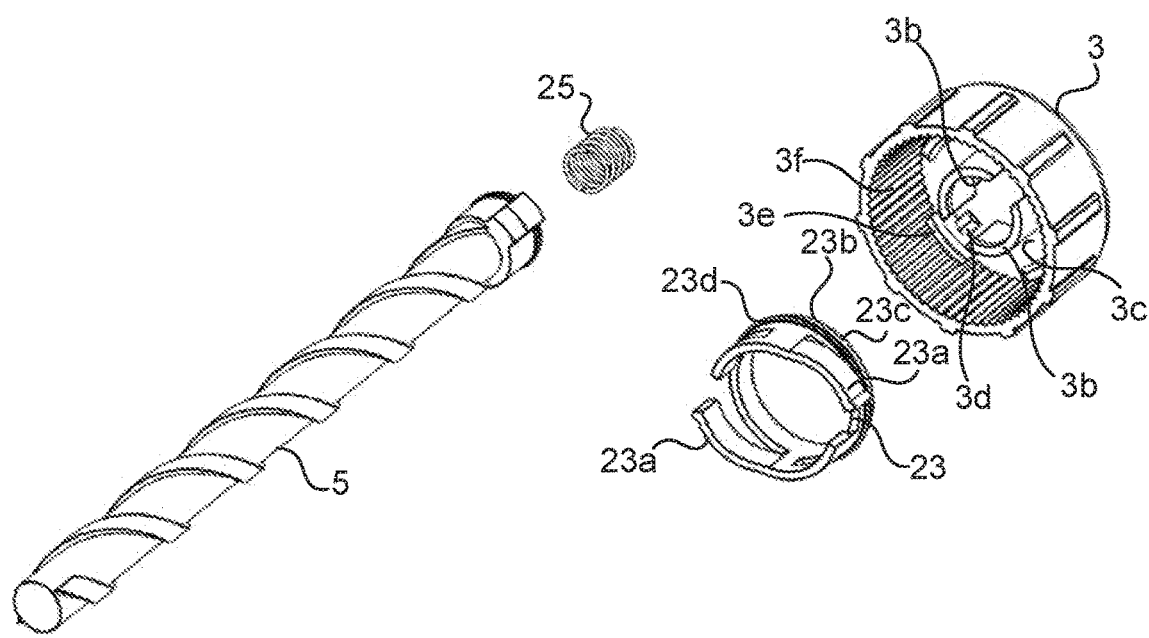
FIG. 2 depicts a perspective view of some of the components of the drive mechanism in FIG. 1.

With reference to FIG. 2, the activation knob 3, the activation rod 5 and the ratchet ring 23 will be explained in more detail.

The activation knob 3 is configured to receive the ratchet ring 23. In particular, the ratchet ring 23 is configured to be received in the central channel 3a of the activation knob 3. The central channel 3a has an inner surface 3c, a bottom surface of the central channel 3a, which is provided with axial protrusions, of which a first axial protrusion 3d is shown in FIG. 2.

The ratchet ring 23 has a distal edge 23b provided with a plurality of first teeth 23c. The first teeth 23c are distributed along the distal edge 23b in the circumferential direction. The first teeth 23c protrude in the axial direction of the drive mechanism 1. The first teeth 23 are configured to engage with the first axial protrusion 3d. The first axial protrusion 3d may hence also have a tooth-like structure in the circumferential direction.

The ratchet ring 23 has a radially outwards extending flange 23d. The holding members 3b are radially flexible and provided with radially inwards extending end portions or flanges 3e configured to hold the flange 23d.

The activation knob 3 is configured to be moved between a first axial position and a second axial position. In the first axial position, the flange 23d engages with the radially inwards extending end portions 3e. The flange 23d is in this position arranged axially in the distal direction beyond the radially inwards extending portions 3e. The activation knob 3 is thereby maintained in the first axial position. The resilient member 25 biases the ratchet ring 23 via the activation rod 5 such that the flange 23d presses against the radially outwards extending end portions 3e so that no play is present between the flange 23d and the radially inwards extending end portions 3e.

Due to the cooperation between the first teeth 23c of the ratchet ring 23 and the axial protrusions 3d, rotation of the activation knob 3 is prevented relative to the ratchet ring 23, which in turn is rotationally locked relative to the housing. Since the activation knob 3 is rotationally locked with the activation rod 5, the activation rod 5 is also rotationally locked.

The activation knob 3 may be pulled, i.e. moved in the distal direction, to move the activation knob 3 to the second axial position. By exerting a large enough pulling force, the flange 23d is moved axially over the radially outwards extending portions 3e, which are flexed radially inwards. The first teeth 23c and the axial protrusions 3d will hence disengage and be spaced apart. The activation knob 3 is thus set in the second axial position relative to the activation rod 5. In the second axial position, the activation knob 3 has been disengaged from the ratchet ring 23, allowing the activation knob 3 to be rotated. The activation rod 5 will thereby also be able to rotate as the activation knob 3 is being rotated.

The central channel 3a of the activation knob 3 has an inner perimeter surface 3c provided with a plurality of second teeth 3f in the circumferential direction. The ratchet ring 23 is provided with flexible arms or ratchet ring arms 23b extending in the radial direction. The arms 23b are configured to engage with the second teeth 3f. Rotation of the activation knob 3 thereby causes audible click sounds as a result of the arms 23b moving in and out between the second teeth 3f. This may enable users with visual impairments to set the dose for a medicament delivery device comprising the drive mechanism 1.

Figure 3:
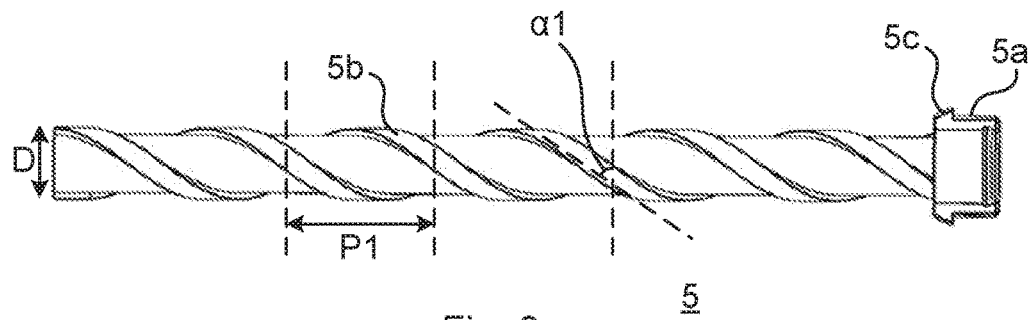
FIG. 3 is a side view of the activation rod shown in FIG. 1.

FIG. 3 shows a side view of the activation rod 5. The external activation rod threads 5b have a first pitch P1. Additionally, the external activation rod threads 5b have a first thread helix angle α1. The activation rod 5 also has a major diameter D.

Figure 4:
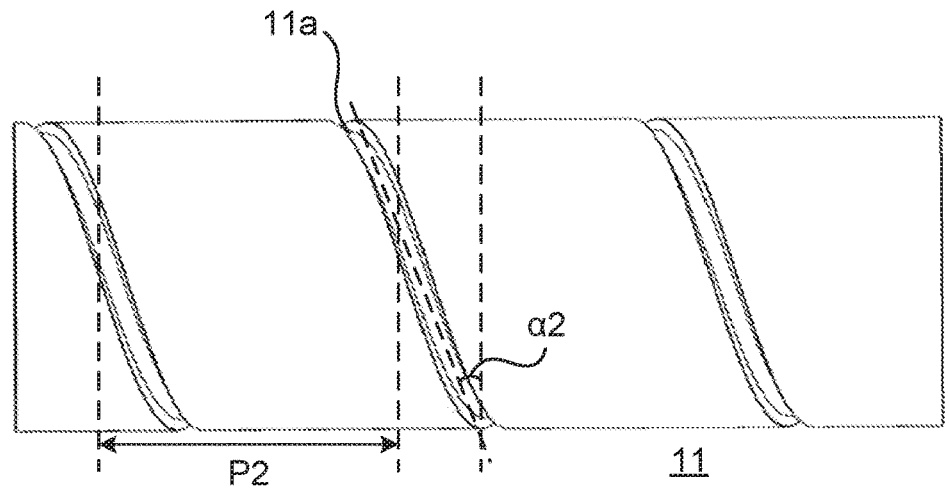
FIG. 4 is a side view of the indicator drum shown in FIG. 1.

FIG. 4 shows a side view of the indicator drum 11. The external indicator drum threads 11a have a second pitch P2. Additionally, the external indicator drum threads 11 have a second thread helix angle α2. The first thread helix angle α1 is preferably larger than the second thread helix angle α2.

The major diameter D of the activation rod 5 is smaller than the inner diameter of the indicator drum 11. The thread helix angles will therefore differ even if the first pitch P1 is equal to the second pitch P2.

The first pitch P1 and the second pitch P2 may be equal, or they may differ. Hereto, the first pitch P1 may be smaller than the second pitch P2 or the first pitch P1 may be larger than the second pitch P12.

Figure 5:
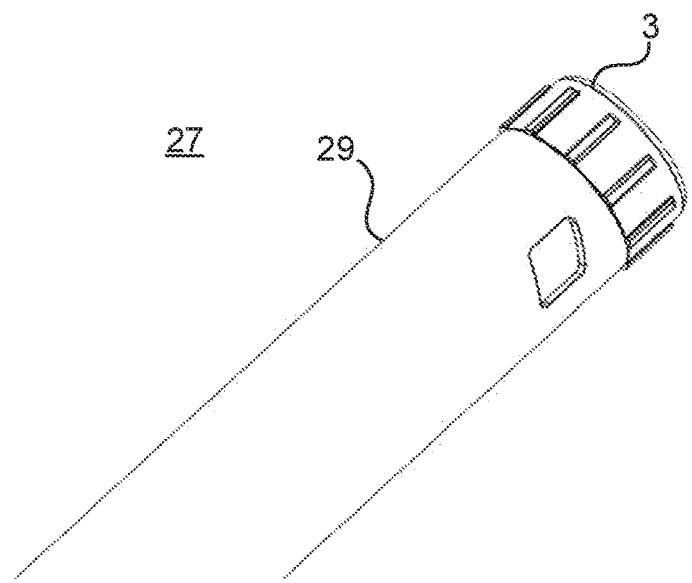
FIG. 5 is a perspective view of a medicament delivery device comprising the drive mechanism in FIG. 1.

FIG. 5 depicts a portion of a medicament delivery device 27 comprising a housing 29 and a drive mechanism 3 arranged in the housing 29.

With reference to FIGS. 6a-6d the operation of the drive mechanism 1 in the medicament delivery device 27 will be described.

Figure 6A:
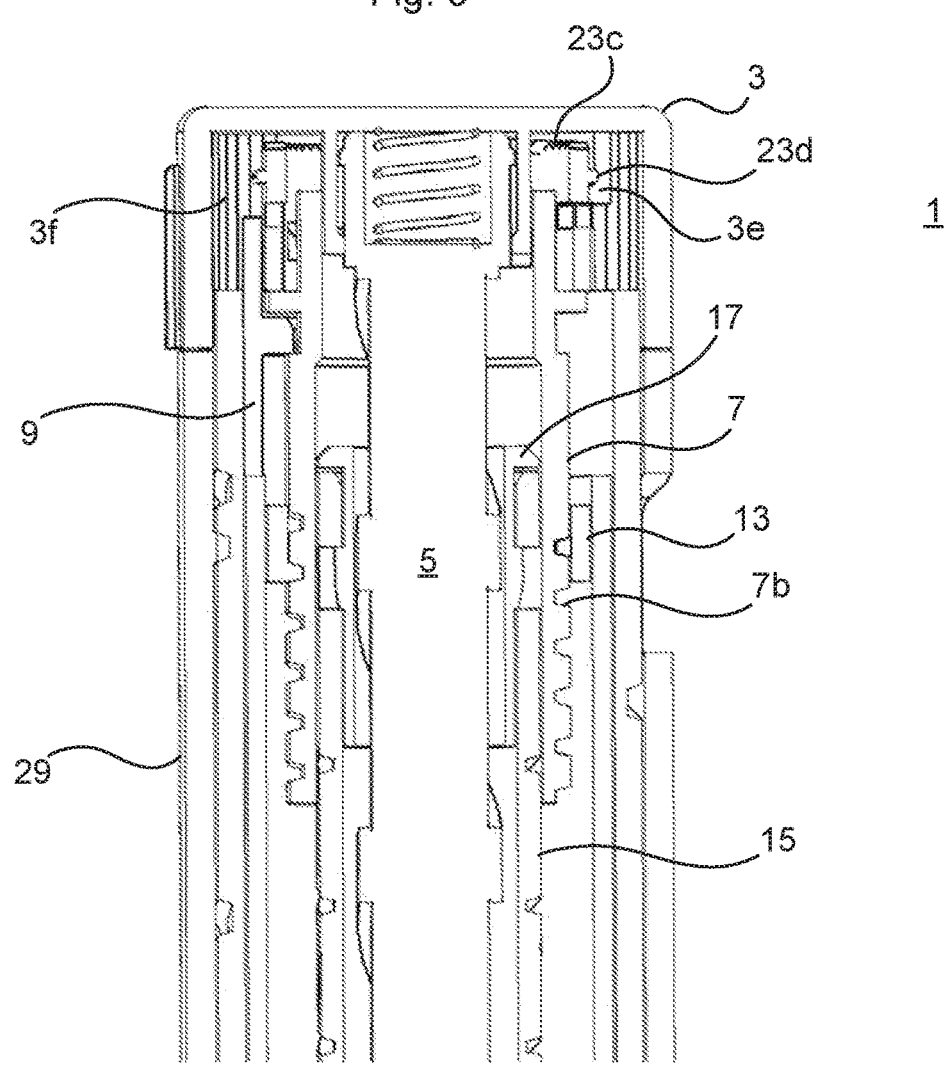
FIGS. 6a, 6b and 6c show longitudinal sections of the medicament delivery device in FIG. 5.

FIG. 6a shows a longitudinal section of a distal end portion of the medicament delivery device 27 before the first dose has been given. In FIG. 6a, the activation knob 3 is in the first axial position. Hereto, the first teeth 23c of the ratchet ring 23 are engaged with the first axial protrusions 3d of the activation knob 3. The remaining dosage ring 13 engages with the dose drum 7 by means of the inner ring threads 13a which are in contact with the external dose drum threads 7b. The remaining dosage ring 13 is in this case located at the distal end of the external dose drum threads 7b.

Figure 6B:
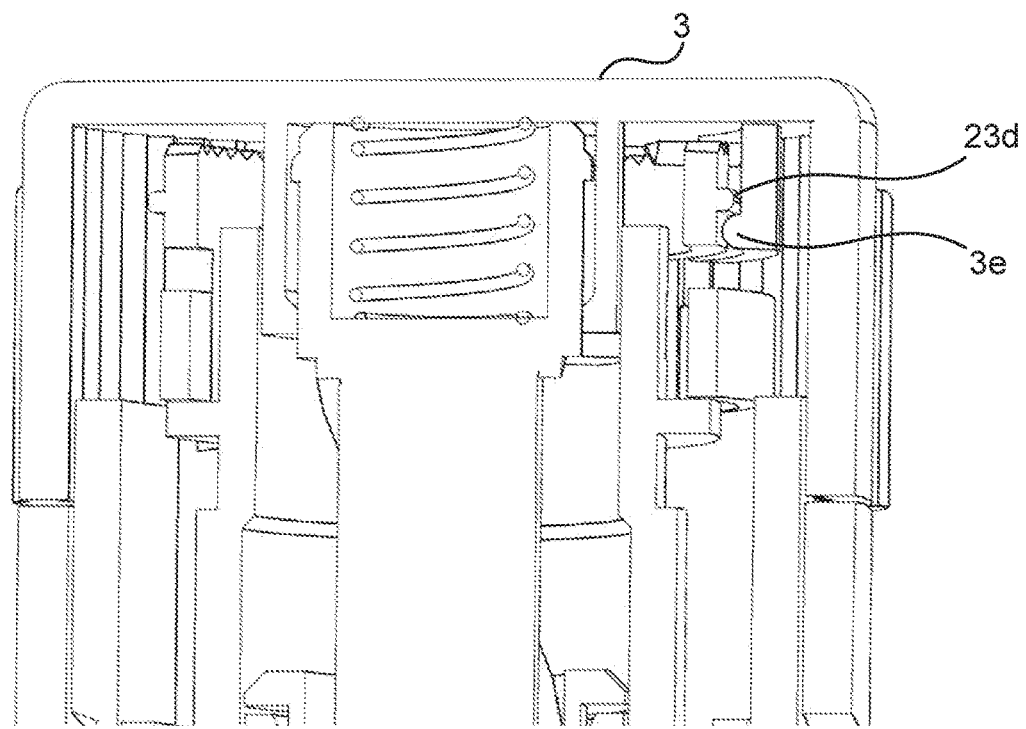

FIG. 6b shows a close-up view of the engagement between the flange 23d the ratchet ring 23 and the radially inwards extending end portions 3e of the activation knob 3.

Figure 6C:
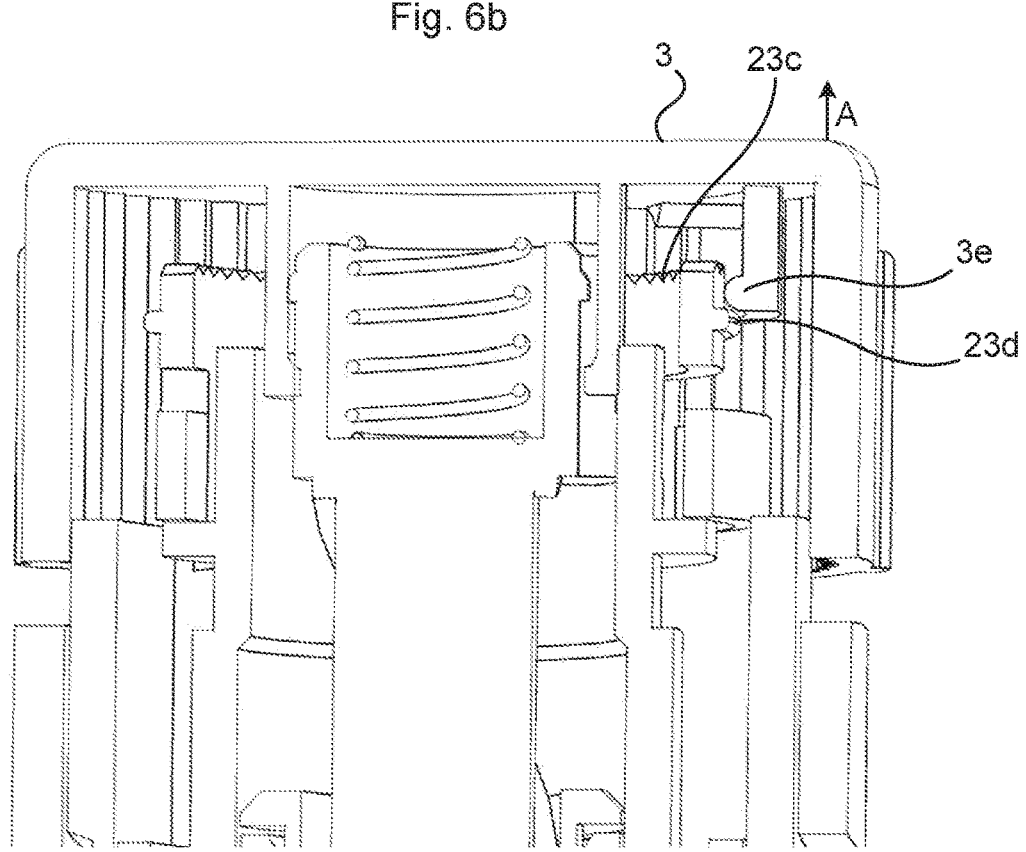

In FIG. 6c, the activation knob 3 has been pulled in the distal direction as shown by the arrow A with a force above a threshold value, causing the snap-lock engagement between the activation knob 3 and the ratchet ring 23 formed by the flange 23d and the radially inwards extending end portions 3e to disengage and the activation knob 3 to be set in the second axial position. The activation knob 3 may thereby be rotated in a first direction, which is the same as the direction of rotation of the plunger rod 15 allowed by the ratchet member 19 and the thread insert 21.

Rotation of the activation knob 3 in the first direction causes rotation of the activation rod 3 in the first direction, since these components are rotationally locked. The dose drum 7 is also rotationally locked with the activation rod 5, causing also the dose drum 7 to rotate. The external activation rod threads 5b of the activation rod 5 cooperate with the threaded insert member inner surface 17b of the insert member 17. The insert member 17 is however rotationally locked with the plunger rod 15. The ratchet member 19 is only able to rotate inside the thread insert 21 in the first direction. The rotation of the activation knob 3 will hence not result in any rotation of the plunger rod 15, which will therefore maintain a fixed position relative to the housing 29. The rotation of the activation knob 3 in the first direction instead results in that the activation knob 3, the activation rod 5, the dose drum 7 are moved in the distal direction relative to the housing 29. The slidable drum 9 is axially locked with the dose drum 7 and will therefore also move distally together with the aforementioned components. The remaining dosage ring 13 will, due to it being axially locked with the slidable drum 9, move along the external dose drum threads 7b. The number of external dose drum threads 7b and their pitch and/or thread helix angle is designed so that it is calibrated to the dose scale of the indicator drum 11.

Figure 6D:
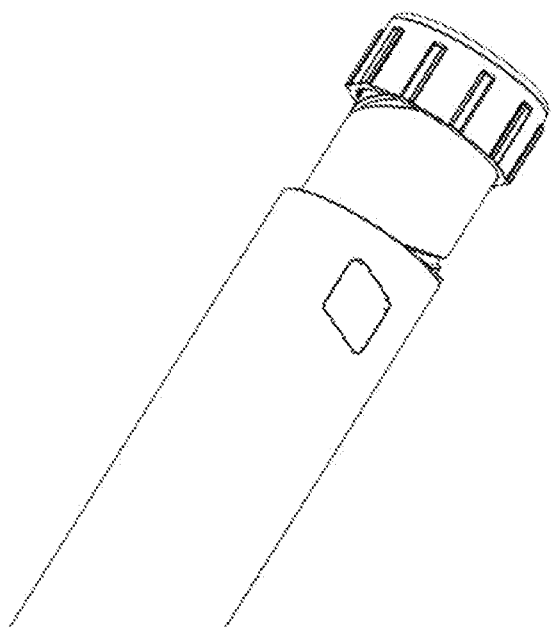
FIG. 6d shows a perspective view of a medicament delivery device with a dose set prior to medicament expulsion.

The indicator drum 11 rests on the heel 9d of the slidable drum 9, causing the indicator drum 11 to be rotated relative to the housing 29, as shown in FIG. 6d as the slidable drum 9 is moved distally to an elevated or extended position relative to the housing. The dosage of a medicament expulsion can thereby be set according to prescription. The activation knob 3 may be rotated also in the second direction in case the indicator drum 11 has been rotated past the desired dose. This will cause the activation rod 5 to rotate and move proximally. The indicator drum 11 will thus also be moved proximally, enabling the user to set the correct dose. Since the activation rod 5 is being rotated, the plunger rod 15 will not be activated. The activation rod 5 will instead be received further in the plunger rod 15.

When a user is to initiate medicament expulsion, the activation knob 3 is pushed in the proximal direction. This causes the activation knob 3 to engage with the ratchet ring 23 so that it obtains the first axial position. The activation knob 3 and the activation rod 5 will thereby be rotationally locked relative to the housing 29. When the activation knob 3 is further pushed, the activation rod 3 and the dose drum 7 will move proximally without being rotated relative to the housing 29. The slidable drum 9 will also be moved in the proximal direction, and so will the indicator drum 11. Since the dose drum 7 is moved back without rotation, the remaining dosage ring 13 will not be rotated relative to the dose drum 7. The remaining dosage ring 13 will thus maintain its position along the external dose drum threads 7b.

The cooperation between the external activation rod threads 5b and the threaded insert member inner surface 17b will due to the non-rotation of the activation rod 5 result in that the insert member 17 is rotated in the first direction. Since the insert member 17 is rotationally locked with the plunger rod 15, the plunger rod 15 will also be rotated in the first direction. The plunger rod 15 will hence move proximally through the thread insert 21 and into a medicament container containing a medicament, causing medicament expulsion from the medicament delivery device 27.

The inventive concept has mainly been described above with reference to a few examples. However, as is readily appreciated by a person skilled in the art, other embodiments than the ones disclosed above are equally possible within the scope of the inventive concept, as defined by the appended claims.

The invention claimed is:

1. A drive mechanism for a medicament delivery device, comprising:
   an activation rod provided with external activation rod threads having a first thread helix angle ($\alpha 1$),
   an activation knob rotationally locked with the activation rod, wherein the activation knob is configured to be moved between a first axial position relative to the activation rod in which the activation knob is prevented from rotation and a second axial position in which the activation knob is allowed to rotate in a first direction,
   an axially slidable drum which is rotationally locked,
   a dose drum rotationally locked relative to the activation rod, wherein the dose drum is configured to rotate relative to the slidable drum,
   an indicator drum provided with external indicator drum threads having a second thread helix angle ($\alpha 2$),
   wherein rotation of the activation knob in the first direction causes concurrent first rotation of the activation rod and the dose drum in accordance with the first thread helix angle ($\alpha 1$) thereby axially displacing the activation knob, the activation rod, the dose drum and the slidable drum in a distal direction, wherein the slidable drum is configured to bring the indicator drum with it causing second rotation of the indicator drum in accordance with the second thread helix angle ($\alpha 2$).

2. The drive mechanism as claimed in claim 1, wherein the first thread helix angle ($\alpha 1$) is larger than the second thread helix angle ($\alpha 2$).

3. The drive mechanism as claimed in claim 1, comprising a remaining dosage ring provided with inner ring threads, wherein the dose drum is provided with external dose drum threads configured to cooperate with the inner ring threads, wherein the remaining dosage ring is rotationally locked with the slidable drum to prevent rotation of the remaining dosage ring relative to the slidable drum, causing the remaining dosage ring to move proximally along the external dose drum threads when the activation knob is rotated in the first direction.

4. The drive mechanism as claimed in claim 1, comprising a plunger rod, and an insert member provided with a threaded insert member inner surface, wherein the plunger rod is configured to rotate only in the first direction, and wherein the insert member is coupled in a rotationally locked manner with the plunger rod and wherein the insert member is configured to receive a proximal end portion of the activation rod, wherein the external activation rod threads (5b) are configured to cooperate with the threaded insert member inner surface, causing the activation rod and dose drum to be axially displaced in the distal direction when the activation knob is rotated in the first direction.

5. The drive mechanism as claimed in claim 4, comprising a thread insert provided with an threaded thread insert inner surface and configured to receive the plunger rod, wherein the plunger rod has external plunger rod threads configured to cooperate with the threaded thread insert inner surface, and a ratchet member configured to be rotationally locked with the plunger rod and to be received by the thread insert allowing rotation of the plunger rod only in the first direction.

6. The drive mechanism as claimed in claim 4, wherein pushing of the activation knob when the activation knob has been axially displaced by rotation of the activation knob in the first direction causes the activation knob to obtain the first axial position, whereby the activation rod and the dose drum are configured to move in the proximal direction without rotation, causing the plunger rod to rotate in the first direction and thereby move in the proximal direction through the thread insert.

7. The drive mechanism as claimed in claim 1, comprising a ratchet ring configured to engage with the slidable drum to rotationally lock the ratchet ring relative to the slidable drum, wherein the ratchet ring is configured to engage with the activation knob in the first axial position to thereby prevent rotation of the activation knob and to disengage from the activation knob in the second axial position.

8. The drive mechanism as claimed in claim 7, wherein the activation knob has an inner surface facing the activation rod, wherein the inner surface is provided with a first axial protrusion and the ratchet ring is provided with first teeth configured to engage with the first axial protrusion to prevent rotation of the activation knob in the first axial position.

9. The drive mechanism as claimed in claim 8, wherein the ratchet ring has a distal edge and the first teeth are distributed along the distal edge.

10. The drive mechanism as claimed in claim 8, wherein the activation knob and the ratchet ring are configured to engage with a snap-fit in the first axial position to maintain the activation knob in the first axial position.

11. The drive mechanism as claimed in any of claim 7, wherein the activation knob is provided with second teeth along its inner perimeter surface and the ratchet ring comprises arms configured to engage with the second teeth to provide audible clicks when the activation knob is rotated in the first direction.

12. The drive mechanism as claimed in claim 1, wherein the indicator drum has an external surface provided with a dosage scale.

13. The drive mechanism as claimed in claim 1, comprising a housing configured to receive the activation rod, dose drum, the slidable drum and the indicator drum, wherein the housing has an inner surface provided with inner housing threads configured to cooperate with the external indicator drum threads and wherein the slidable drum is rotationally locked with the housing.

14. A medicament delivery device comprising:
   a housing, and
   a drive mechanism as claimed in claim 1 arranged in the housing.

15. The medicament delivery device as claimed in claim 14, wherein the slidable drum is rotationally locked with the housing.

16. The medicament delivery device as claimed in claim 14, wherein the housing has an inner surface provided with inner housing threads configured to cooperate with the external indicator drum threads.

17. A drive mechanism for a medicament delivery device, comprising:
   an activation rod comprising activation rod threads;
   an activation knob rotationally locked with the activation rod;
   a non-rotating axially slidable drum;
   a dose drum rotationally locked relative to the activation rod, where the dose drum is configured to rotate relative to the slidable drum;
   an indicator drum comprising indicator drum threads; and
   a plunger rod comprising a hollow portion configured to accept and allow axial movement of a proximal end of the activation rod;
   wherein rotation of the activation knob in a first direction causes concurrent first rotation of the activation rod and the dose drum to axially displace the activation knob, the activation rod, the dose drum and the slidable drum in a distal direction, where the axial movement of the slidable drum causes simultaneous movement the indicator drum which causes a second rotation of the indicator drum.

18. The drive mechanism of claim 17, wherein the activation rod threads comprise a first pitch and indicator drum threads have a second pitch, where the first pitch and second pitch are different.

19. The drive mechanism of claim 17, further comprises an insert operatively connected to the plunger rod and having an inner surface threadedly connected to the external activation rod threads.

20. The drive mechanism of claim 17, wherein the activation knob moves relative to the activation rod between a first axial position and a second axial position, where in the first axial position the activation knob cannot rotate and when in the second axial position the activation knob can rotate in a first direction.

* * * * *